(12) United States Patent
Baust et al.

(10) Patent No.: US 10,054,262 B2
(45) Date of Patent: Aug. 21, 2018

(54) PRESSURIZED SUB-COOLED CRYOGENIC SYSTEM

(71) Applicant: CPSI Holdings LLC, Owego, NY (US)

(72) Inventors: John M. Baust, Owego, NY (US); Joshua T. Smith, Owego, NY (US); Anthony T. Robilotto, Binghamton, NY (US); Jennie F. McKain, Endicott, NY (US)

(73) Assignee: CPSI Holdings LLC, Owego, NY (US)

( * ) Notice: Subject to any disclaimer, the term of this patent is extended or adjusted under 35 U.S.C. 154(b) by 384 days.

(21) Appl. No.: 14/687,449

(22) Filed: Apr. 15, 2015

(65) Prior Publication Data

US 2015/0300569 A1 Oct. 22, 2015

Related U.S. Application Data

(60) Provisional application No. 61/980,396, filed on Apr. 16, 2014.

(51) Int. Cl.
*F17C 1/00* (2006.01)
*F17C 5/02* (2006.01)

(52) U.S. Cl.
CPC . *F17C 1/00* (2013.01); *F17C 5/02* (2013.01)

(58) Field of Classification Search
CPC .............. A61B 18/02; A61B 2018/0262; F25B 2309/021; F25B 2309/02; F17C 5/02; F17C 1/00
See application file for complete search history.

(56) References Cited

U.S. PATENT DOCUMENTS

| | | | |
|---|---|---|---|
| 4,339,253 A | 7/1982 | Caetani et al. | |
| 5,392,608 A | 2/1995 | Lee | |
| 5,452,582 A * | 9/1995 | Longsworth | A61B 18/02 606/24 |
| 5,758,505 A | 6/1998 | Dobak et al. | |
| 5,910,104 A * | 6/1999 | Dobak | A61B 18/02 600/121 |
| 6,039,730 A * | 3/2000 | Rabin | A61B 18/02 606/21 |
| 6,085,545 A | 7/2000 | Johnston | |
| RE40,868 E | 8/2009 | Ryba et al. | |
| 8,361,059 B2 * | 1/2013 | Abboud | A61B 18/02 606/22 |
| 2005/0261753 A1* | 11/2005 | Littrup | A61B 18/02 607/96 |
| 2010/0256621 A1* | 10/2010 | Babkin | A61B 18/02 606/21 |

* cited by examiner

*Primary Examiner* — Brian King
(74) *Attorney, Agent, or Firm* — Hoffman Warnick LLC

(57) ABSTRACT

A cryogenic system as well as a method of generating a pressurized, sub-cooled mixed-phase cryogen and a method of delivering such a cryogen to a cryoprobe are disclosed. In an embodiment, the cryogenic system includes a reservoir containing a liquid cryogen and a sub-cooling coil immersed in the liquid cryogen. The cryogen is supplied to the sub-cooling coil and is cooled under pressure to produce a pressurized mixed phase cryogen within the sub-cooling coil. This pressurized mixed phase cryogen is provided via supply line to a cryo-device for use.

20 Claims, 11 Drawing Sheets

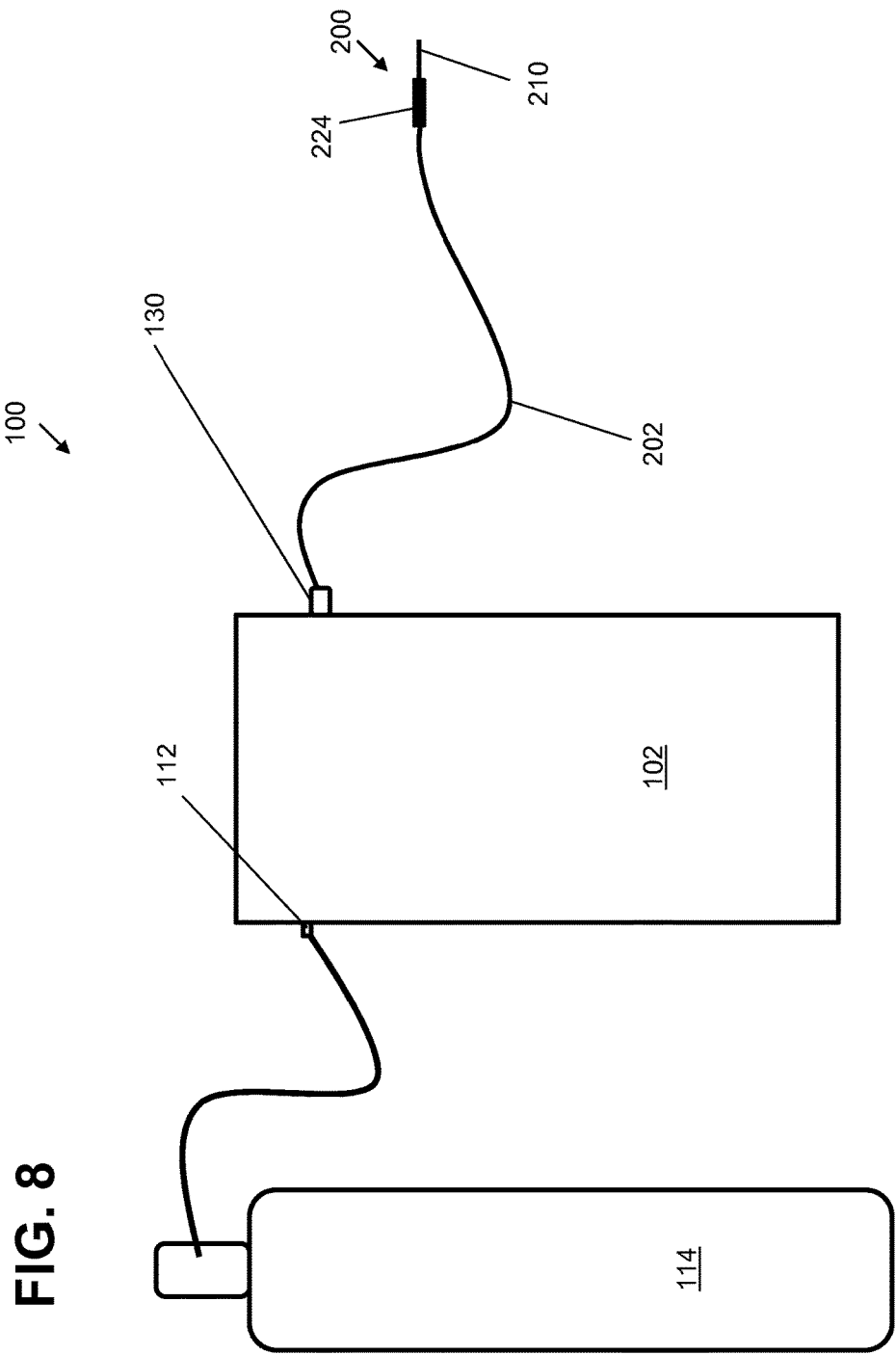

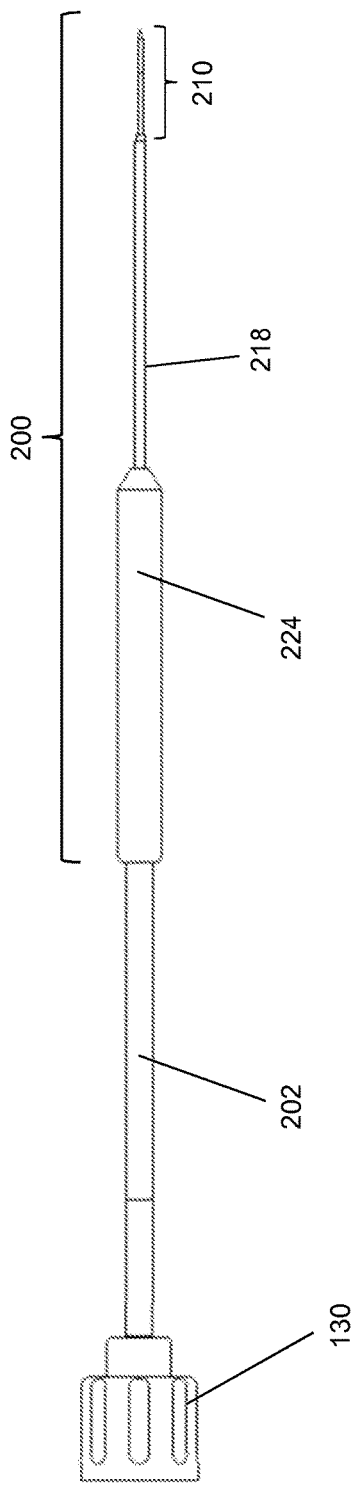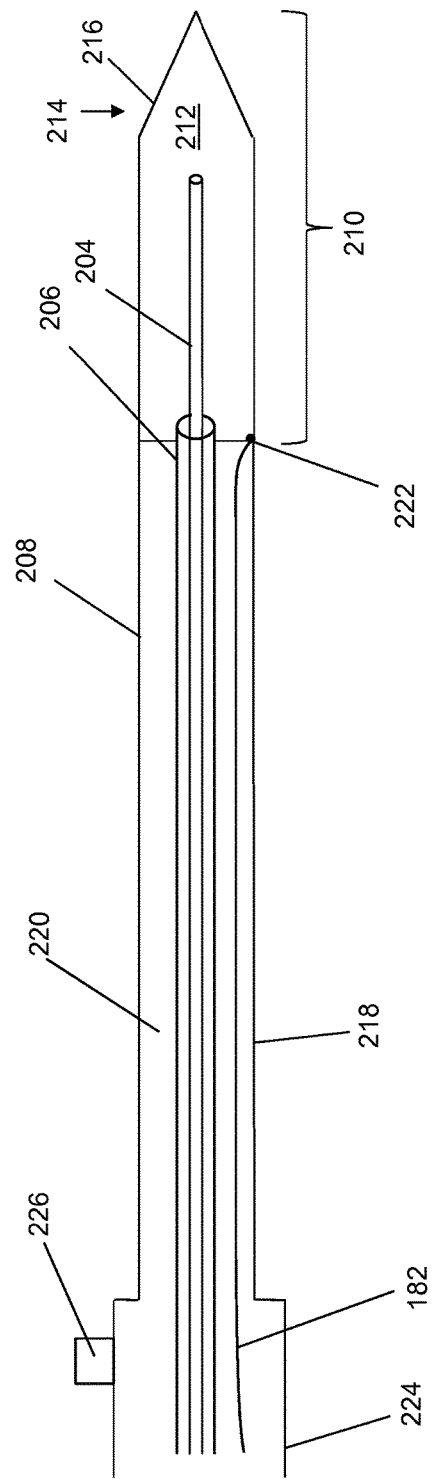

PRESSURIZED SUB-COOLED CRYOGENIC SYSTEM

CROSS REFERENCE TO RELATED APPLICATIONS

This application claims the benefit of U.S. Provisional Patent Application No. 61/980,396, filed Apr. 16, 2014, which is hereby incorporated herein as though fully set forth.

BACKGROUND OF THE INVENTION

The invention relates generally to cryogenic medical devices. More particularly, the invention relates to a cryogenic medical device for delivering a pressurized sub-cooled, mix-phased cryogen to a cryoprobe.

With the strong movement in the medical community toward the use of minimally invasive therapies, ablation therapies are becoming more prevalent. Cryotherapy (or cryoablation) is a minimally invasive method of treating disease by freezing an area to ablate a target tissue. Cryotherapy provides an alternative to radical surgery, radiation therapy, chemotherapy, and hyperthermal ablation. Advantages of ablation therapies relative to these conventional therapies include, for example, precise eradication of targeted tissue, decreased hospitalization time, limited postoperative morbidities, shortened return interval to activities of daily living, reduced severity and incidence of side effects, and reduced overall treatment cost.

Cryotherapy is currently used to treat numerous disease states including but not limited to: benign and cancerous tumors of the prostate, kidney, liver, pancreas, bone, and skin, as well as cardiovascular disease, retinal detachment, pain management, and other illness/disease states. In many applications, it is desirable to be able to selectively freeze a very small area to a very low temperature without affecting the temperature of surrounding tissues and organs.

Cryogens that have been used for ablation procedures include liquid nitrogen ($LN_2$), critical nitrogen (CN), supercritical nitrogen (SCN), nitrous oxide (NO), argon gas (Ar), and carbon dioxide ($CO_2$). Current systems and devices have focused on delivery of the liquid cryogen through the use of low to moderate pressure (15-450 psi) on the entire system, piston/bellows compression to drive fluid movement, creation of critical or supercritical states through heat and pressurization (500-1200 psi), or alternatively, the use of cryogen gases such as nitrous oxide, carbon dioxide, and argon under extremely high pressures, e.g., 3,000-6,000 psi in Joule-Thomson based systems. Each of these systems has significant drawbacks.

In the case of high pressure, gas cryogen Joule-Thomson based systems, ineffective cooling and limited ability to drive ablative temperatures (e.g., −40° C.) into target tissues is a significant inherent weakness. Further, Joule-Thomson systems rely on the use of costly rare gases such as argon and nitrous oxide, delivered under high pressures, which limits the use of these systems.

Liquid systems, on the other hand, provide colder temperatures and greater freezing (heat extraction) capacity, but are slow to achieve a target temperature and often result in over-freezing of tissue. This results in unwanted collateral damage to surrounding tissue. Finally, systems utilizing cryogens in a critical or supercritical state, while providing a more powerful and quicker freeze, require complicated device architecture and larger cryogen reservoirs, and face challenges in the ability to run multiple probes in complex sequences.

BRIEF DESCRIPTION OF THE INVENTION

A first aspect of the disclosure provides a cryogenic system comprising a reservoir containing a liquid cryogen, and a sub-cooling coil immersed in the liquid cryogen. A cryogen is supplied to the sub-cooling coil and is cooled within the sub-cooling coil under pressure to produce a pressurized mixed phase cryogen. The pressurized mixed phase cryogen is delivered to the cryo-device by a supply line.

A second aspect of the disclosure provides a method of generating a pressurized, mixed-phase, sub-cooled cryogen. The method comprises providing a reservoir containing a liquid cryogen and a sub-cooling coil immersed in the liquid cryogen, the sub-cooling coil having an input end and an output end not immersed in the liquid cryogen; and introducing a pressurized gas cryogen to the input end of the sub-cooling coil. The method further comprises the steps of cooling the pressurized gas cryogen within the sub-cooling coil; and collecting the pressurized gas cryogen at an output end of the sub-cooling coil.

A third aspect of the disclosure provides a method of providing a pressurized, mixed-phase, sub-cooled cryogen for use in a cryoprobe, the method comprising the steps of: providing a reservoir containing a liquid cryogen and a sub-cooling coil immersed in the liquid cryogen, the sub-cooling coil having an input end and an output end not immersed in the liquid cryogen; introducing a pressurized gas cryogen to the input end of the sub-cooling coil; cooling the pressurized gas cryogen within the sub-cooling coil to form the pressurized, mixed-phase, sub-cooled cryogen; delivering the pressurized, mixed-phase, sub-cooled cryogen to a tip of the cryoprobe via a supply line; and returning the used pressurized, mixed-phase, sub-cooled cryogen from the tip of the cryoprobe to the reservoir.

These and other aspects, advantages and salient features of the invention will become apparent from the following detailed description, which, when taken in conjunction with the annexed drawings, where like parts are designated by like reference characters throughout the drawings, disclose embodiments of the invention.

BRIEF DESCRIPTION OF THE DRAWINGS

FIG. 8 shows a schematic rendering of a system including a cryoprobe and an external pressurized cryogen cylinder in accordance with an embodiment of the invention.

FIGS. 9-10 show a probe tip in accordance with an embodiment of the invention.

Figure 1:
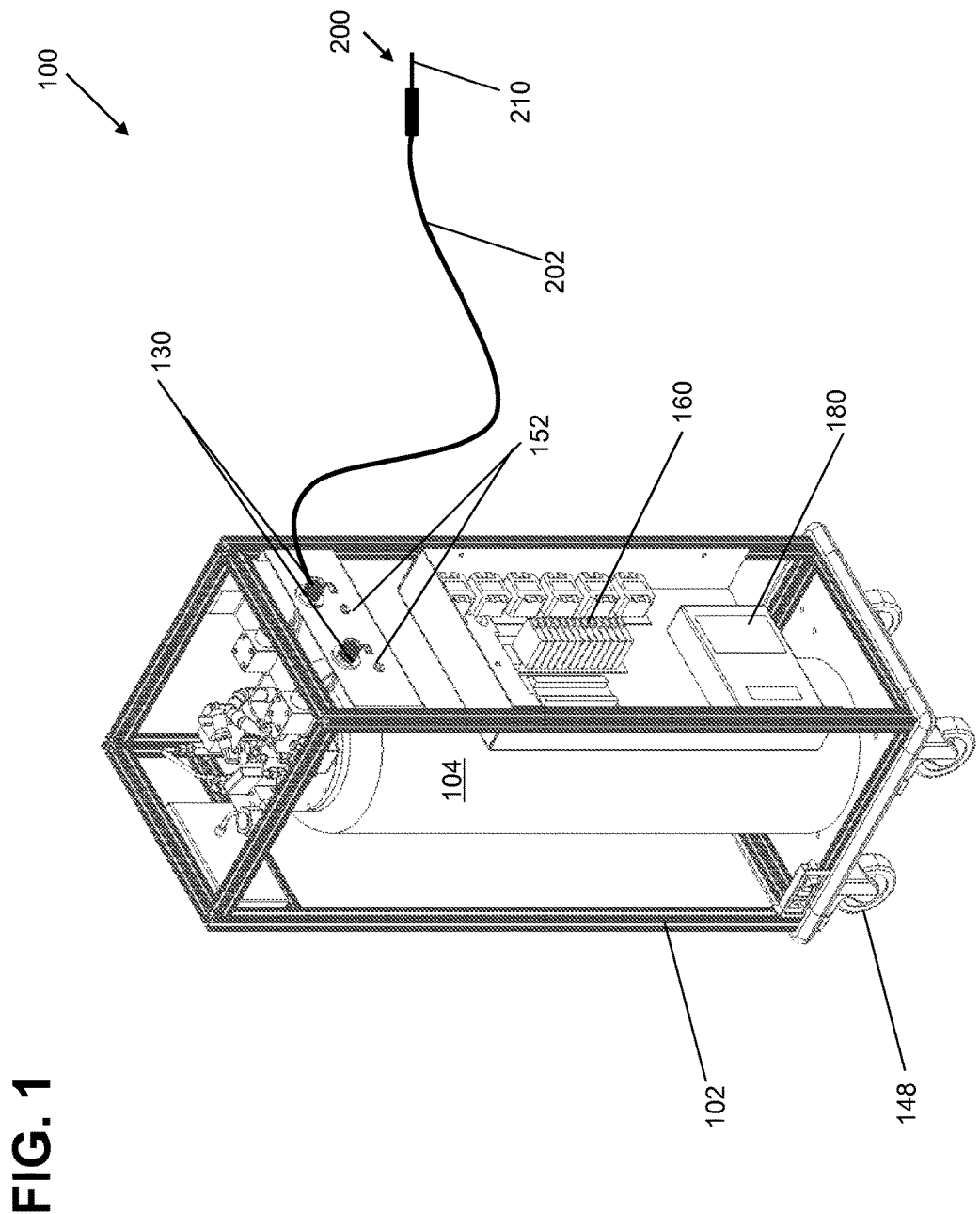
FIG. 1 shows a perspective view of a system in accordance with an embodiment of the invention.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

Embodiments of the present invention are described below in reference to their application to the operation of a cryogenic system, shown in FIGS. 1-10. Although embodiments of the invention are illustrated relative to a closed loop cryogenic probe with recirculating cryogen fluid, it is understood that the teachings are equally applicable to other cryogenic system configurations, including those with semi-closed loop cryogen circulation. Further, at least one embodiment of the present invention is described below in reference to a nominal size and including a set of nominal dimensions and parameters, including temperature and pressure. However, it should be apparent to those skilled in the art that the present invention is likewise applicable to any suitable cryogenic system. Further, it should be apparent to those skilled in the art that the present invention is likewise applicable to various scales of the nominal size and/or nominal dimensions.

FIG. 1 illustrates a closed-loop cryogenic system 100 in which the pressurized sub-cooled cryogen is delivered to a cryoprobe 200 for use during a procedure, and is contained in both the supply and return stages. The cryogenic system 100 includes a system enclosure 102, which may include, e.g., sidewalls and top and bottom panels. A sub-cooling reservoir 104, which may be, e.g., a vacuum-insulated dewar, may be provided within the enclosure 102.

Figure 2:
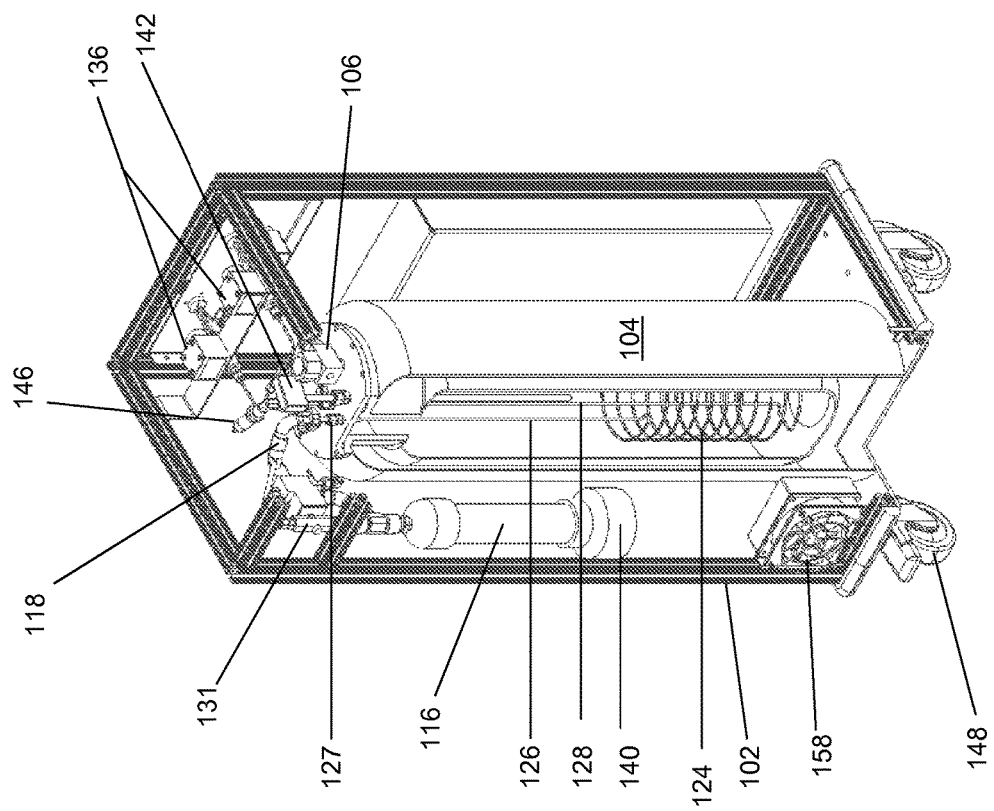
FIG. 2 shows a partial cutaway perspective view of a system in accordance with an embodiment of the invention.

As shown in FIG. 2, the sub-cooling reservoir 104 may include a valved cryogen supply port 106 for filling the reservoir 104. The fill valve 106 connects the reservoir 104 with the sub-cooling reservoir fill line 108 (FIG. 4), and controls flow of liquid cryogen into the reservoir 104 for reservoir filling during operation. Prior to operation, the cryogenic sub-cooling reservoir 104 may be filled with liquefied gas cryogen such as, e.g., liquid nitrogen, argon, oxygen, helium, hydrogen, propane, alcohol, ethylene glycol, propanediol, or other cryogens known in the art, by a cryogenic fill tank (not shown), which may include one or more liquid cryogen cylinders, and which would connect to the sub-cooling reservoir fill line 108 prior to the connection of the pressurized gas cylinder. After filling, the reservoir 104 may be detached from the fill tank, and the reservoir 104 may be closed at the valved cryogen supply port 106 to form a closed reservoir 104. The reservoir 104 may be made of, e.g., stainless steel or any other material known for providing a vacuum insulated vessel, or may be insulated by foam or insulating material.

Once the reservoir 104 has been filled, a pressurized cryogenic gas supply is provided. This may be done in any of a number of ways. In one example, a pressurized cryogenic gas supply is connected to the high pressure cryogenic gas input connection 112 as illustrated in FIG. 8, and the system is ready for use. The pressurized cryogenic gas supply may include one or more pressurized cylinders 114 (external in FIG. 8; internal in FIG. 3) linked together in series or in parallel. In various embodiments, the pressurized cryogen cylinder(s) 114 may be integrated into the system enclosure 102 as shown in, e.g., FIG. 3, or may be external to the system enclosure 102 as shown in FIG. 8. Some embodiments may contain both an internal and an external pressurized cryogen gas cylinder 114 simultaneously. Alternatively, with reference to FIG. 3, a cryogenic gas supply may be connected to the low pressure cryogenic gas input connection 110. The low pressure cryogen gas may be delivered to the compressor 120 via the low pressure cryogen gas input connection 110 from any source including the atmosphere, external gas cylinders, gas supply lines within a facility, etc., and the low pressure cryogen gas may be conducted from input connection 110 to compressor 120 by compressor input line 111. A compressor gas input solenoid 113 and compressor gas input pressure regulator 115 may be provided along compressor gas input line 111, upstream of compressor 120. The compressor gas input solenoid 113 and compressor gas input pressure regulator 115 function to control the flow and input pressure of the low pressure cryogen gas into the compressor 120. The compressor gas input solenoid 113 can be opened or closed to direct flow of the gas cryogen into the compressor 120 as well as prevent backflow (leakage) of the compressed cryogen from the system when the compressor 120 is not in use. The compressor gas input regulator 115 is designed to limit the pressure (maximum or minimum) of the input cryogen gas within the input pressure specification range of the compressor 120. Compressor 120, which may be provided within the enclosure 102, may be used to compress the gas to achieve a higher pressure, e.g., nominally between about 13.79 MPa and about 41.37 MPa (between about 2,000 and about 6,000 psi); or about 20.69 MPa and about 31.03 MPa (about 3,000 to about 4,500 psi). After being compressed by compressor 120, the pressurized cryogen gas may be supplied to pressurized cylinder 114 by connection line 117, which may include cryogen gas flow valve 119 and pressure check valve 122 in order to prevent back flow of pressurized cryogen gas into the compressor 120 during and following cryogen gas pressure cylinder pressurization. Pressure cylinder 114 may further be provided with an output pressure regulator 121 and a pressure sensor 144. The output pressure regulator 121 enables control of the pressure of the cryogen gas exiting the pressure cylinder 114. For example, the pressure of the cryogenic gas contained within the pressure cylinder will vary during operation from about 41.37 MPa (6,000 psi) to about 6.89 MPa (1,000 psi). While the pressure within pressure cylinder 114 varies, the pressure cylinder regulator 121 can be set to a constant out pressure, thereby providing for delivery of a constant cryogen flow and pressure range to the sub-cooling coil 124. The pressure sensor 144 is is utilized to monitor the pressure of the cryogen gas within the pressure cylinder 114 when the system is turned on. This includes during re-pressurization via the compressor 120, during operation for delivery of the cryogen through the sub-cooling coil 124 and to the probe 200 as well as during maintenance, holding, or other such operations. In another embodiment, the compressor 120 with or without additional pressurization cylinders may be contained within a separate satellite unit to the system to which the system can be connected for recharging when not in use. Further, an integrated pressurized cryogen gas cylinder 114 may be refilled and/or re-pressurized by direct connection to an external high pressure gas source via the high pressure cryogen gas input connection 112 (FIG. 3), or by a combination of direct connection and compressor-based embodiments.

In some embodiments, the system may be pressurized during operation, and/or may include a vent muffler assembly 116 (FIGS. 2, 5) which may include a pressure bleeder valve, coil vent solenoid 131, coil vent line 129 (FIGS. 2, 4, 5) and/or muffler. The vent muffler assembly 116 may be fluidly coupled to the reservoir 104 by a reservoir vent line 118 (FIGS. 2, 4, 5), and may be used to vent the system enclosure 102 to the surrounding environment to prevent excess pressure buildup during operation or from static boil off of the liquid cryogen during non-use periods.

Referring back to FIG. 2, reservoir 104 may include at least one sub-cooling coil 124 submerged within the internal cavity thereof. The coil 124 can be any diameter and be made of any metal or plastic. For example, the coils 124 may be made of tubing made from copper, stainless steel, titanium, or a variety of plastics, and may be coiled to an overall coil diameter of about 5.1-25.4 cm (about 2-10 inches), although smaller or larger coils can be used. The internal diameter of the tubing used in the coil can be any dimension depending on the desired system configuration (number of ports, run time of system, dimension of probes used, etc.). While any tubing diameter may be utilized, an example of a typical tubing internal diameter range is about 0.5-3.2 mm (about 0.020-0.125 inch), or about 0.76-1.78 mm (about 0.03-0.07 inch).

Figure 3:
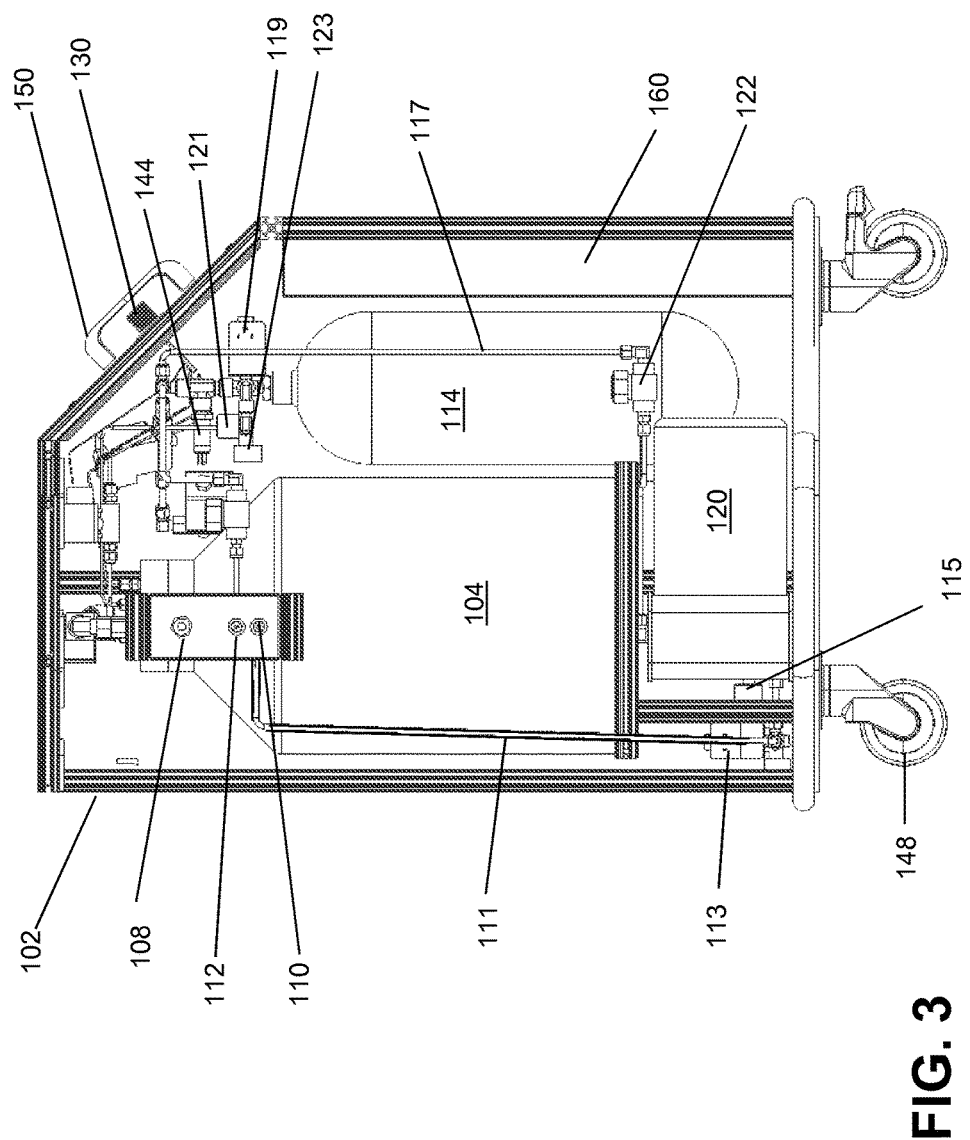
FIG. 3 shows a side cross section view of a system including an internal reservoir and a pressure cylinder in accordance with an embodiment of the invention.

At an input end, the sub-cooling coil 124 is fluidly connected with cryogen gas input line 126 tubing, which is connected via a cryogen gas input connection 127 to a pressurized cryogen gas cylinder 114 (FIG. 3). The cryogen gas may be supplied to the sub-cooling coil 124 via either an integrated or external cylinder 114 of cryogen gas as previously described. Any size or pressure cryogen gas cylinder 114 may be used, although in one example, the cylinder may contain nitrogen gas at about 16.55 MPa, 31.23 MPa, or 41.37 MPa (about 2,400 psi, 4,500 psi, or 6,000 psi) starting pressure. The cryogen gas input line 126 may further include a pressure regulator 121 (FIG. 3) for adjusting the pressure of the incoming cryogen gas delivered to the sub-cooling coil 124. An exemplary incoming cryogen gas pressure may be nominally between, e.g., about 6.89-10.34 MPa (about 1,000-1,500 psi), and may particularly be about 8.96 MPa (about 1,300 psi). For example, once cryogen flow is established through the cryoprobe 200 (FIGS. 8-10) during a procedure (about 1-2 minutes), the incoming cryogen pressure may be maintained or may be decreased to any pressure, e.g., nominally about 3.45-5.17 MPa (about 500-750 psi) to conserve cryogen gas supply and extend cryogen gas supply cylinder 114 usage time. In this regard, the incoming cryogen gas supply pressure may be increased or decreased at any point of a procedure as desired in support of a variety of scenarios including in order to compensate for changes in heat load, conservation of pressure, driving of critical isotherms deeper into a target tissue, creation of a larger or smaller freeze area, to activate and/or deactivate any number of cryoprobes, etc. Upon depressurization (emptying) of the cryogen gas supply cylinder 114, an additional cylinder(s) can be connected and the process can be repeated or any number of cylinders may be connected and operated individually or in combination with one another.

At an output end of the sub-cooling coil 124, the coil 124 may be fluidly connected with a cryogen output line 128 (FIGS. 2, 6), which is connected via supply line 134 (FIG. 5, 6) to a probe or catheter 200 (FIGS. 1, 8-10) via a probe connection port 130 coupling connection (FIGS. 1, 3-5).

Although only one sub-cooling coil 124 is shown in the figures, other embodiments may include any number of sub-cooling coils 124 fluidly connected with a pressurized cryogen gas supply and a probe connection port 130 in similar fashion.

The sub-cooling coil 124 is immersed in the liquid cryogen contained within the reservoir 104 as shown in FIG. 2. The liquefied gas cryogen may be, for example, liquid nitrogen, argon, oxygen, helium, hydrogen, propane, alcohol, ethylene glycol, propanediol, or another cryogen as known in the art. Regardless of the specific cryogen used, each pressurized cryogenic gas contained in cylinder 114 and used in the system must be matched with an appropriate second cryogen within the cryogenic cooling reservoir 104 to provide an appropriate temperature of the pressurized gas such that the sub-cooling process within the sub-cooling coil 124 results in an ultra-cold fluid (gas, liquid, mixed phase) but not a solid, which would result in blockage of flow through the sub-cooling coil 124. In another embodiment, an ultra-cold refrigeration system 186 (FIG. 12) or other means of sub-cooling the sub-cooling reservoir 104 in order to sub cool the gas contained within the sub-cooling coil 124 to a desired temperature may be utilized in place of or in conjunction with a cryogen cooling fluid.

Figure 4:
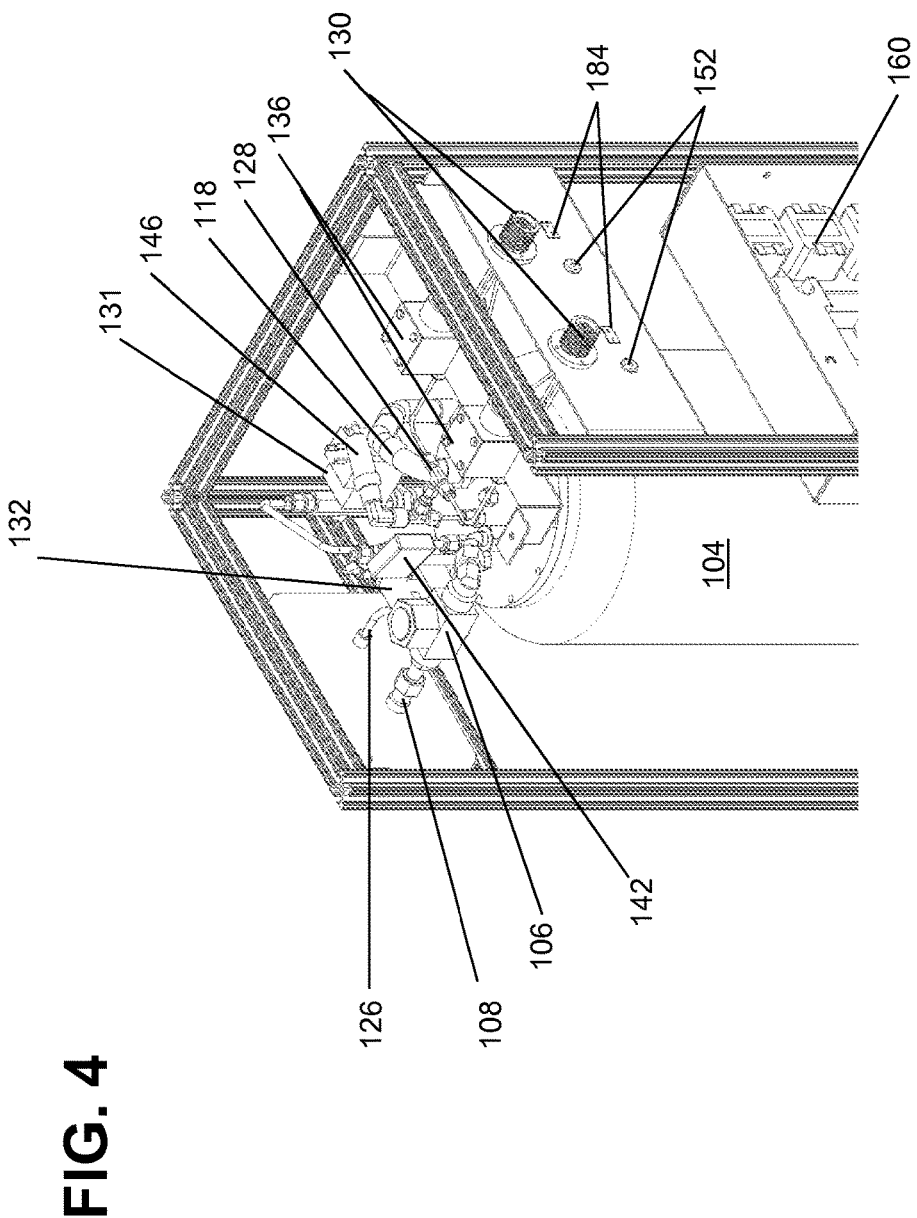
FIG. 4 shows a partial cutaway perspective view of a system in accordance with an embodiment of the invention.
Figure 5:
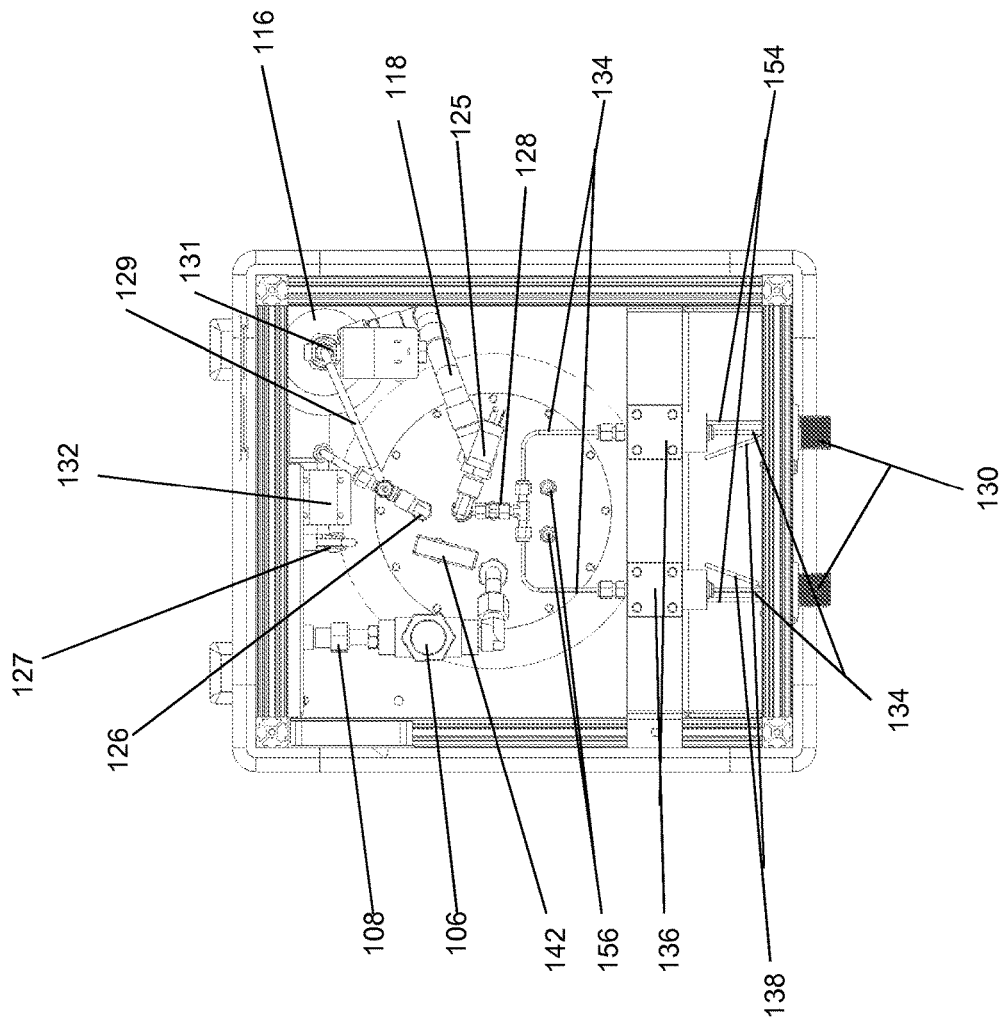
FIG. 5 shows a top view of a system in accordance with an embodiment of the invention.
Figure 6:
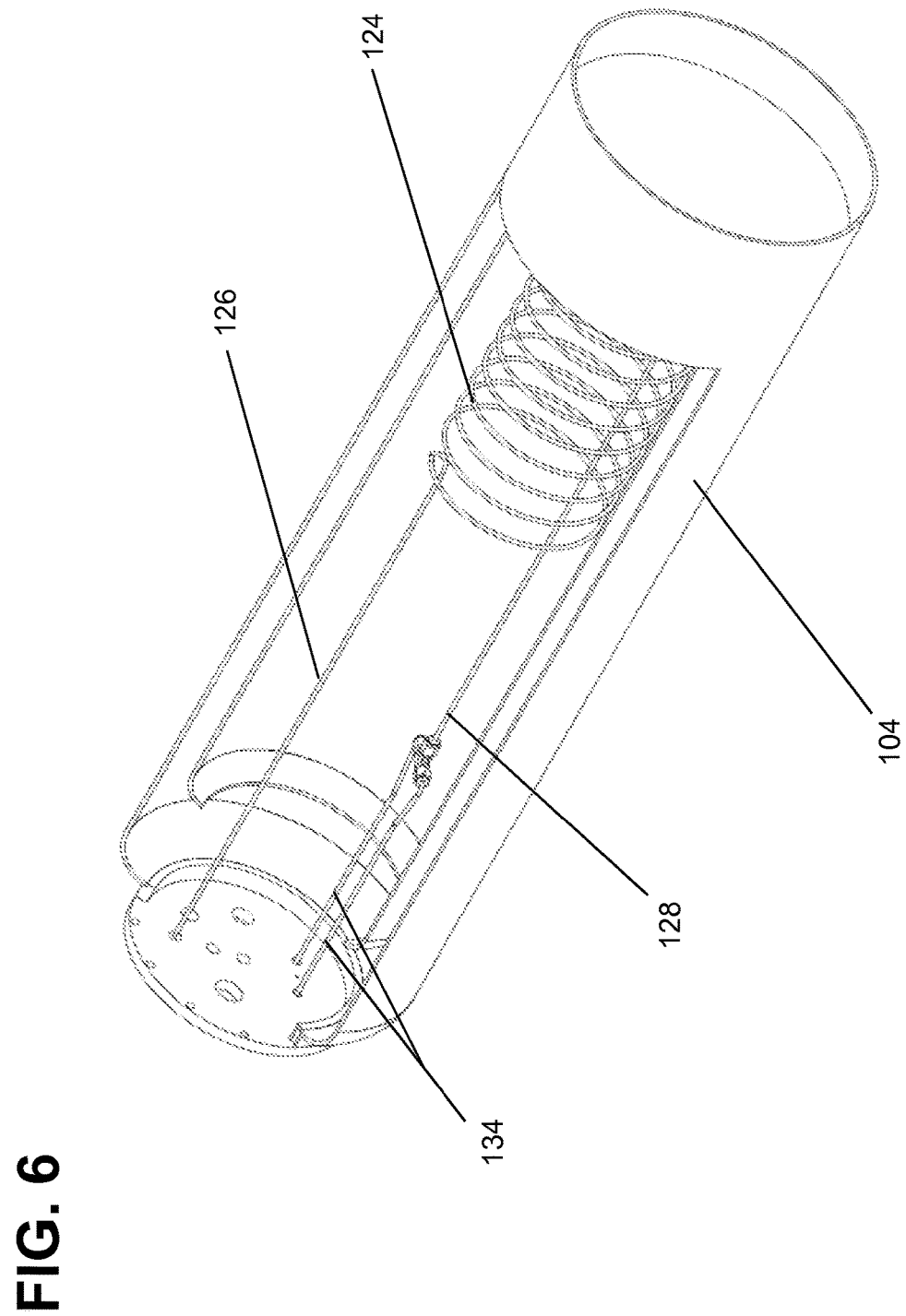
FIG. 6 shows a partial cutaway perspective view of a cryogenic sub-cooling reservoir and sub-cooling coil in accordance with an embodiment of the invention.
Figure 7:
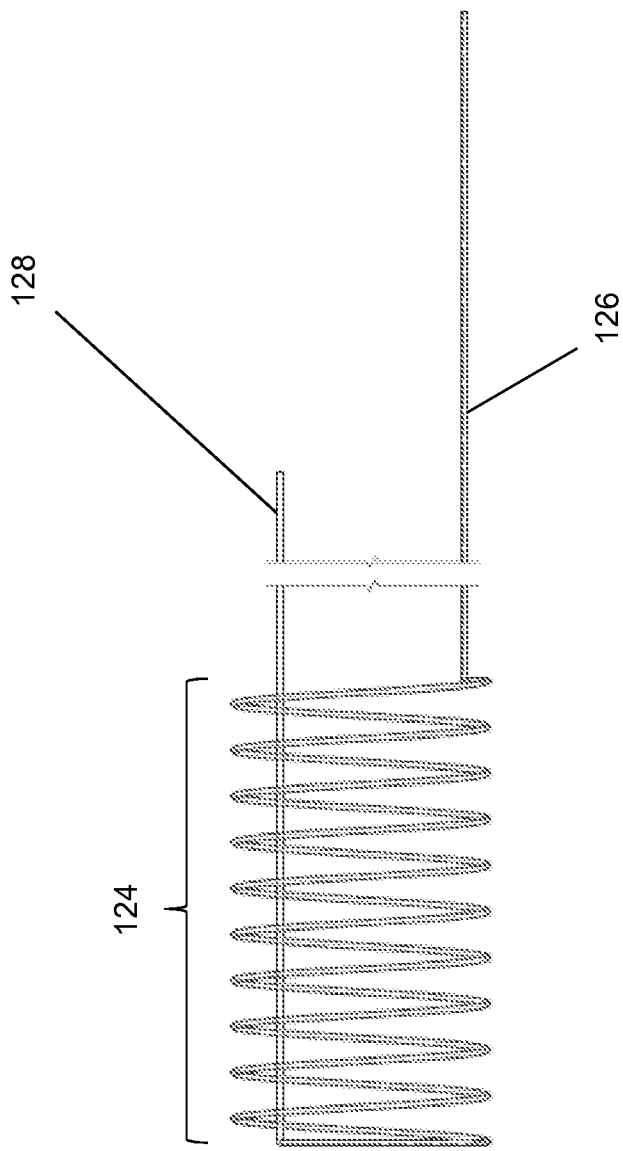
FIG. 7 shows a side view of a sub-cooling coil in accordance with an embodiment of the invention.

As shown in FIGS. 4-5, a pressurized cryogen/sub-cooling coil gas flow control valve and a pressure regulator assembly 132 control the flow of the pressurized cryogen into the sub-cooling coil 124. Pressurized cryogen gas inbound into the coil may be in the range of about 6.89-10.34 MPa (about 1,000-1,500 psi), however a pressure range of about 3.45-17.24 MPa (about 500-2,500 psi) or greater can also be used. Once the pressurized cryogen enters the sub-cooling coil 124 and passes through the immersed portion of the coil 124, the cryogen is sub-cooled by heat exchange between the gas within the coil 124 and the surrounding liquid cryogen bath in the reservoir 104. The submerged sub-cooling coil 124 acts as a heat exchanger in which the outer surface of the sub-cooling coil 124 is in direct contact with the cryogen in the reservoir 104, and the internal surface of the sub-cooling coil 124 is in direct contact with the pressurized cryogenic gas. This results in the cooling and condensation of the cryogen gas within the inner lumen of the sub-cooling coil 124, thereby creating pressurized sub-cooled mixed phase cryogen (liquid and gas) for delivery to the probe 200 (FIGS. 1, 8-10). The mixed phase pressurized cryogen has an increased ability to absorb heat (heat extraction capacity) relative to the cryogen gas that was initially introduced into the sub-cooling coil 124.

In one example, where nitrogen gas is provided to the sub-cooling coil 124, the pressurized mixed phase sub-cooled cryogen is referred to as $psN_2$. In this example, the liquid nitrogen within the sub-cooling reservoir 104 may be maintained at a temperature of about −196° C. When the pressurized $N_2$ gas is passed through the sub-cooling coil 124, heat is extracted from the $N_2$ gas and the cryogen is cooled to between −196° C. and about −150° C. In various further embodiments, the cryogen may be cooled to between about −185° C. and about −160° C., or between about −170° C. to −160° C., or below about −160° C. Various other temperature ranges may be applicable where cryogens other than nitrogen are used.

As a result of the creation of the mixed phase cryogen within the sub-cooling coil 124, there is typically a drop in the output pressure of the sub-cooling coil 124. This drop varies depending on input pressure and volume (flow), and characteristics of sub-cooling coil 124 volume (tubing or chamber length and diameter). For example, using an approximately 6.10 m length of 3.18 mm outer diameter (20 ft. length of 0.125 inch outer diameter) copper tubing which is coiled and submerged in a liquid nitrogen ($LN_2$) bath in reservoir 104, an approximately 1.38 MPa (200 psi) pressure drop will result from a nitrogen ($N_2$) gas input pressure of 8.96 MPa (1,300 psi). This example results in a coil output $psN_2$ pressure of about 7.58 MPa (1,100 psi) for delivery to the cryoprobe.

The pressurized ultra-cold mixed phase cryogen is then delivered at a controlled rate from the sub-cooling coil 124 to a probe or catheter 200. The cryogen passes from the sub-cooling coil 124 to the cryogen output line 128, which leads to a supply line or a plurality of supply lines 134 to probe connection port(s) 130 (FIGS. 1, 3-5, and 8). A single sub-cooling coil 124 (FIG. 6) may be connected to one or two ports 130 (FIG. 3) for supporting the operation of one or two probes or catheters 200, although any number or configuration of coils 124 and ports 130 can be supported. Pressurized mixed-phase, sub-cooled cryogen may then be released through a high pressure cryogen flow solenoid or valve 136 (FIGS. 4 and 5) for delivery into one or more flexible cryoprobes 200, shown in FIG. 8, such that the cryogen flows rapidly to the probe 200 via an umbilical line 202. It is noted that the term "umbilical," as used herein, is used to refer to any flexible or inflexible tubing used to fluidly couple the probe 200 with probe connection ports 130 on the system enclosure 102. In various embodiments, the umbilical line 202 may extend up to about 3 meters (about 10 feet) or more, although any length may be used. Shorter dimensions may be better suited where attached tubing, removable, detachable, or disposable parts are integrated in the design. Cryoprobe 200 may also include a probe handle 224 disposed in line between the umbilical line 202 and the probe shaft 218. Probe handle 224 may be used to hold and operate cryoprobe 200, and may include features such as, e.g., a control button 226. The control button 226 can be configured to control any number of functions including on/off of cryogen flow to the probe 200, setting/changing or monitoring of cryogen pressure during, prior to and following operation, and setting and monitoring a desired set point temperature for the probe.

The cryogen flows with minimal heat gain or friction from the enclosure to the distal tip 214 of the probe 200 as a result of the pressure head created by the continuous pressurized cryogen gas coming into the sub-cooling coil 124 during operation. At the distal end or tip 214 of the probe shaft, the internal tubes, i.e., the supply and return tubes 204, 206 respectively, come into contact with the probe outer sheath 208, and create a defined region or freeze zone 210 of ultra-cold temperature to cool and freeze the target tissue region. The catheter or probe 200 is designed to carry the cryogen under various pressures as well as at varying temperatures.

In the boiling chamber 212 at the probe tip 214, cryogen pressure drops due to the increased volume of the chamber and the outflow restriction. Within the boiling chamber 212, the cryogen interacts with the probe tip 214, and heat is absorbed (nucleate boiling) along the inner surface of the probe sheath 208 at tip 214. Micro-bubbles of cryogen gas condense back into a liquid, and the warmed cryogen reverts to pressurized mixed phase cryogen as it exits the probe tip 214 through the return line 206 and returns via the umbilical line 202 to the sub-cooling cryogen reservoir 104. It is noted that the supply and return lines 204, 206 may continue through umbilical line 202 (FIG. 9) in similar substantially concentric fashion as illustrated in probe 200 in FIG. 10, or may convert to being substantially parallel within umbilical line 202.

Once the system is activated and the mixed phase cryogen is created in the sub-cooling coil 124, the cryogen flow dynamic from the sub-cooling coil 124 to the probe tip 214 occurs rapidly, typically creating ice on the outer surface 216 of the probe tip 214 within a few seconds, e.g., about 2 to about 30 seconds. An ultra-cold probe surface 216 temperature of, e.g., about −160° C. may be attained within about 30-90 seconds. These time estimates vary depending on the probe, attachment configuration, and heat load to which the probe is exposed. The flow of cryogen from the sub-cooling coil 124 to the probe tip 214 is controlled by a high pressure cryogenic solenoid valve 136 which is interconnected between the output line 128 of the sub-cooling coil 124 and the probe connection port 130 (FIGS. 4 and 5), e.g., in line with the supply line 134. Once the instruments are in place, the cryosurgical procedure can be performed with freeze times in ranges of, e.g., about 15 seconds to about 5 minutes or longer. Upon emptying of the first pressurized cryogen gas cylinder 114, a second cylinder may be activated allowing the freezing process to continue or be repeated.

In various embodiments, a variety of structural configurations of probes, catheters, and tips may be used, having a variety of sizes, shapes, dimensions, and configurations. Further, the probe or catheter used may be a single use disposable or a multi-use/reusable part capable of being sterilized between individual patient treatments. The freeze zone 210 may be created where the internal components of the probe contact the outer sheath 208 at a distal end 214 of the probe 200, such as a distal end in which the supply line 204 and return line 206 convene at the freezing zone 210 of the tip 214. In other embodiments, the distal end of the probe 200 may be needle-like, blunt-tipped, or balloon tipped, may include a closed loop, or may be of another probe or catheter tip design.

In any of these embodiments, the cryogen is circulated from the enclosure 102 to the tip 214 of the probe or catheter 200, and then returned to the enclosure 102. The supply line 204 extends to a distance into the tip 214 beyond the extension of return line 206 such that cryogen delivered to the tip circulates within the sealed confines of the boiling chamber 212 when the catheter or probe 200 is engaged for the procedure. The supply line 204 can extend any length or distance into the tip 214. The probe and catheter shaft 218 and tip 214 may be composed of any flexible or rigid material including metallic, plastic, or ceramic compositions. Similarly, a balloon-like structure within the sheath 208 may cause the outer sheath 208 to inflate and deflate for cryogenic procedures.

The return line 206 or outer sheath 208 may be connected to a vacuum pump (not shown) within the enclosure 102 near the compressor 120 to evacuate the probe 200 at any point prior to, during or following a procedure. A vacuum line 138, which may be within or separate from the probe connection port 130, may be provided for this purpose, as shown in FIG. 5. A vacuum may be formed within the probe 200 upon sealing the cryoprobe vacuum lumen 220 (FIG. 10) and mechanically drawing a vacuum through the vacuum line 138. The vacuum line 138 may connect to its own vacuum system or may be provided in combination with the vacuum pump of the cryosystem.

As noted, the cryogen is returned from the cryoprobe 200 by a return line 206 which runs through the umbilical line 202 and re-enters the system enclosure 102 at a probe connection port 130. The returning cryogen may be used in several different ways. In a first embodiment, illustrated in FIG. 5, the returning cryogen is delivered by the return line 154 into the sub-cooling reservoir 104, via cryogen return port(s) 156. In such a case, the return line 154 is vented into the main sub-cooling reservoir 104 for collection and reuse to refill/maintain the sub-cooling reservoir 104. Return of the cryogen to the main reservoir 104 allows the collected cryogen to extend the operation time of the system.

In a second possible embodiment, the return line 154 may return the cryogen as bulk fluid into a cryogen gas pressure cylinder 114 (FIG. 3). In such an embodiment, cryogen is collected in the cryogen gas pressure cylinder 114, and when collection is complete, the valve 119 is closed. The cylinder 114 pressurizes to a set pressure via either passive or active boiling and evaporation of the cryogen within the contained pressure cylinder 114. The cylinder 114 may, e.g., passively pressurize to a preset pressure which may be, e.g., between 13.79-41.37 MPa (2,000-6,000 psi) nominally. The preset pressure may be controlled by a pressure relief valve 123 positioned on the cylinder to prevent over-pressurization of the cylinder 114. Once re-pressurization is complete, the cylinder is ready for subsequent use.

In a third, semi-closed loop embodiment, the returning cryogen may be passed through a heat exchanger venting system 140 to warm and evaporate the cryogen prior to release into the atmosphere, as shown in FIG. 2. In such an embodiment, the heat exchanger venting system 140, which may include a fan and heater assembly 158, may be used as a heat exchanger to warm any cryogen vapor that is vented from the system prior to venting, to avoid formation of fog in the environment outside the enclosure 102.

Regardless of which combinations of the foregoing features are employed in a given embodiment, a plurality of valve-controlled ports and sensors may be provided for monitoring and electronically controlling temperatures, pressures, and flow rates of cryogen passing through the sub-cooling unit; as well as for monitoring pressurized cylinder pressure; sub-cooling reservoir liquid cryogen level; pressure, flow and temperature of the attached probe or catheter; time of operation; and other parameters. Collectively, the valves and controls, including heaters, sensors, motors, or gauges may be controlled by a control and monitoring center 160.

Figure 11:
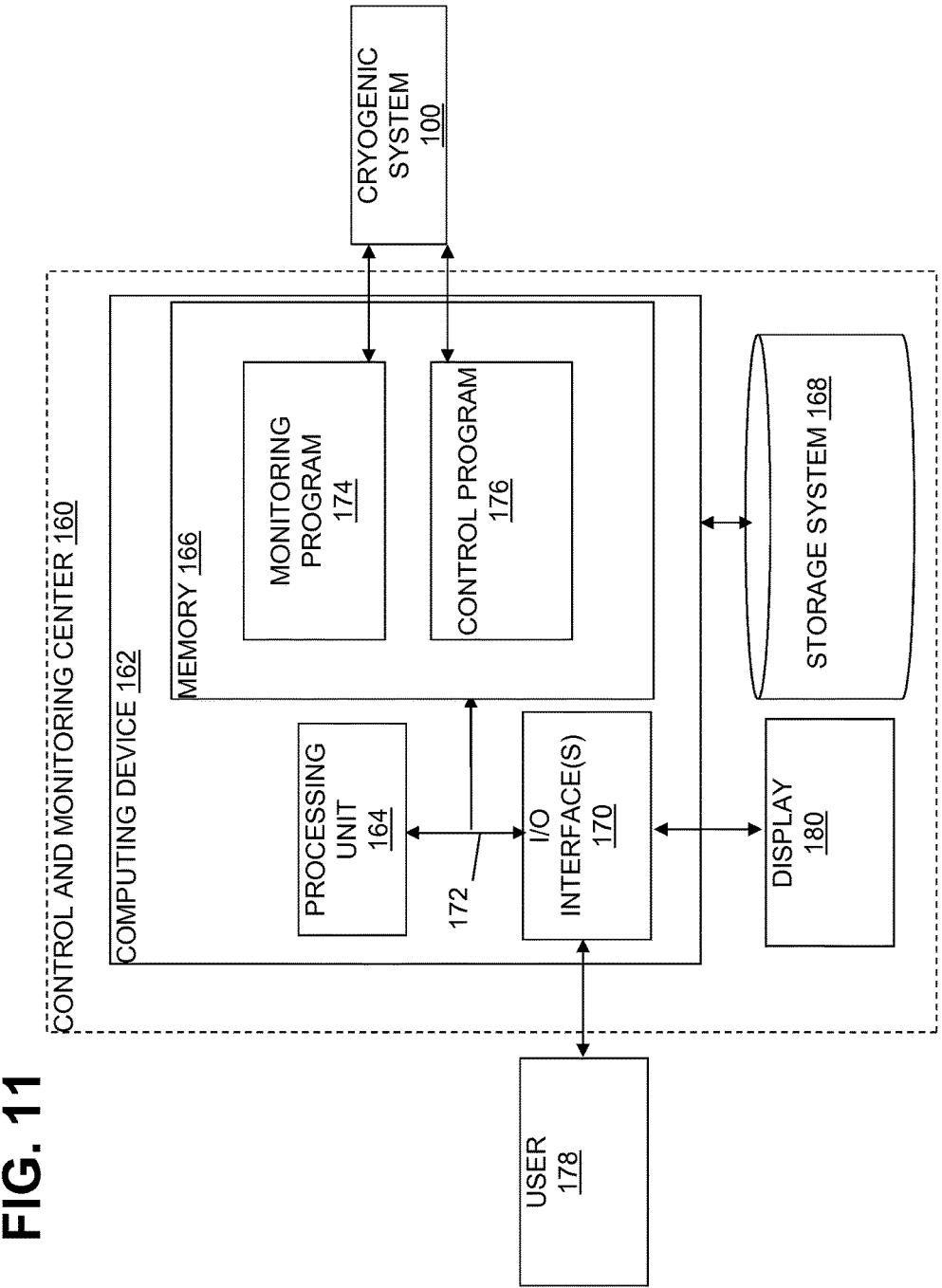
FIG. 11 shows a schematic illustration of the control and monitoring system portion of the cryogenic system of, e.g., FIG. 1, in accordance with an embodiment of the invention.

As shown in FIG. 11, control and monitoring center 160 may further include a computing device 162 that includes a software program stored in a memory thereof, which when executed, carries out various control and monitoring functions of the system. Computing device 162 performs processes described herein in order to monitor system parameters such as time (e.g., elapsed), temperature, pressure, and fluid flow rates, and to control, adjust, or regulate the system parameters in accordance with user objectives.

Computing device 162 is shown including a processing unit 164 (e.g., one or more processors), a memory 166, a storage system 168 (e.g., a storage hierarchy), an input/output (I/O) interface component 170 (e.g., one or more I/O interfaces and/or devices), and a communications pathway 172. In general, processing unit 164 executes program code, such as monitoring program 174 and control program 176, which are at least partially fixed in memory 166. To this extent, processing unit 164 may comprise a single processing unit, or be distributed across one or more processing units in one or more locations.

Memory 166 can also include local memory, employed during actual execution of the program code, bulk storage (storage 168), and/or cache memories (not shown) which provide temporary storage of at least some program code in order to reduce the number of times code must be retrieved from bulk storage 168 during execution. As such, memory 166 may comprise any known type of data storage and/or transmission media, including magnetic media, optical media, random access memory (RAM), read-only memory (ROM), a data cache, a data object, etc. Moreover, similar to processing unit 164, memory 166 may reside at a single physical location, comprising one or more types of data storage, or be distributed across a plurality of physical systems in various forms, included, but not limited to a primary host site and/or a subscription backup site.

While executing program code, processing component 164 can process data, which can result in reading and/or writing transformed data from/to memory 166 and/or I/O component 170 for further processing. Pathway 172 provides a direct or indirect communications link between each of the components in control and monitoring system 160. I/O interface component 214 can comprise one or more human I/O devices, which enable a human user 178 to interact with control and monitoring system 160 and/or one or more communications devices to enable a system user 178 to communicate with control and monitoring system 160 using any type of communications link.

To this extent, monitoring program 174 and control program 176 can manage a set of interfaces (e.g., graphical user interface(s), application program interface, and/or the like) that enable human and/or system users 178 to interact with monitoring and control programs 174, 176. Further, monitoring program 174 can manage (e.g., store, retrieve, create, manipulate, organize, present, etc.) the data collected during monitoring using any solution.

In any event, control and monitoring system 160 can comprise one or more general purpose computing articles of manufacture 162 (e.g., computing devices) capable of executing program code, such as monitoring and control programs 174,176, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, monitoring and control programs 174, 176 can be embodied as any combination of system software and/or application software. As discussed herein, monitoring program 174 enables control and monitoring system 160 to implement monitoring of operational parameters of cryogenic system 100 or tissue on which system 100 is being used. This may include, e.g., display of operational parameters on a display 180. Control program 176 enables control and monitoring system 160 to implement user-initiated or automatic adjustments to operational parameters, which may be made either independently or in dependence upon operational parameters as monitored by monitoring program 174.

In order to provide data to monitoring program 174, sensors located throughout cryogenic system 100 may monitor operating parameters such as pressure, temperature, and fluid level in the reservoir 104, pressure of the cryogen at any point within the cylinder(s) 114, coil(s) 124, probe(s) 200 or reservoir 104, and/or may measure other metrics as may be desired. The sensors may further monitor and provide feedback information control for various valves and components via the control and monitoring center 160. One example of such feedback control is that of control of pressurization of one or more components such as the pressurized cryogen gas cylinder(s) 114 to maintain the system within defined safety ranges of the various components, parts and materials utilized in the system 100.

One possible example of system monitoring may include use of a reservoir level sensor 142 (FIGS. 2, 4-5) to monitor the fill level of the liquid cryogen within the sub-cooling reservoir 104 to assure the sub-cooling coil 124 is submerged. In another example, pressure sensors 144 (FIG. 3) are utilized on the pressurized gas supply cylinders 114 to assure that the incoming cryogen gas pressure is within proper operating ranges. For instance, when nitrogen is used as the cryogen, pressurized cryogen gas cylinder pressure may be 6.89 MPa (1,000 psi) or greater (typically between about 6.89 MPa (1,000 psi) and about 41.37 MPa (6,000 psi)). Pressure sensors 146 may also be utilized to monitor the incoming pressure to the sub-cooling coil 124 to assure it is within the desired operating range. For instance, when nitrogen gas is used, a coil input pressure of between about 6.89 MPa (1,000 psi) and about 10.34 MPa (1,500 psi) is typically targeted. Coil sensors 125 (FIG. 5) may also be located on the output line 134 of the sub-cooling coil 124 to monitor cryogen flow, pressure, temperature or other desired parameter.

Various temperature sensors 222 (FIG. 10) may also be utilized within the system to monitor temperature of the mixed phase cryogen, sub-cooling reservoir 104, probe tip 214, or at any other location. In the probe 200, temperature sensors 222 may be thermocouples, and may be used to monitor probe 200 temperature. A display 180 (FIG. 1) on or coupled to the enclosure 102 may be used in connection with the temperature sensors 222 or other sensors (e.g., pressure sensors) to display operational parameter readings. Any of the valves 106, 122, 132, 136 and sensors 144, 146, 222 may be automated to enable a controlled and consistent operation of the cryogenic system (e.g. computer controlled operation through the electronically controlled, e.g., by control program 176 (FIG. 11) valves). As such, each of the valves and sensors may be in electrical signal communication with control and monitoring center 160. For example, temperature sensors 222 in probe 200, shown in FIG. 10, may be connected to control and monitoring center 160 by wires 182, which may be coupled at the enclosure 102 with probe sensor interface connections 184, and within the enclosure to control center 160.

Figure 12:
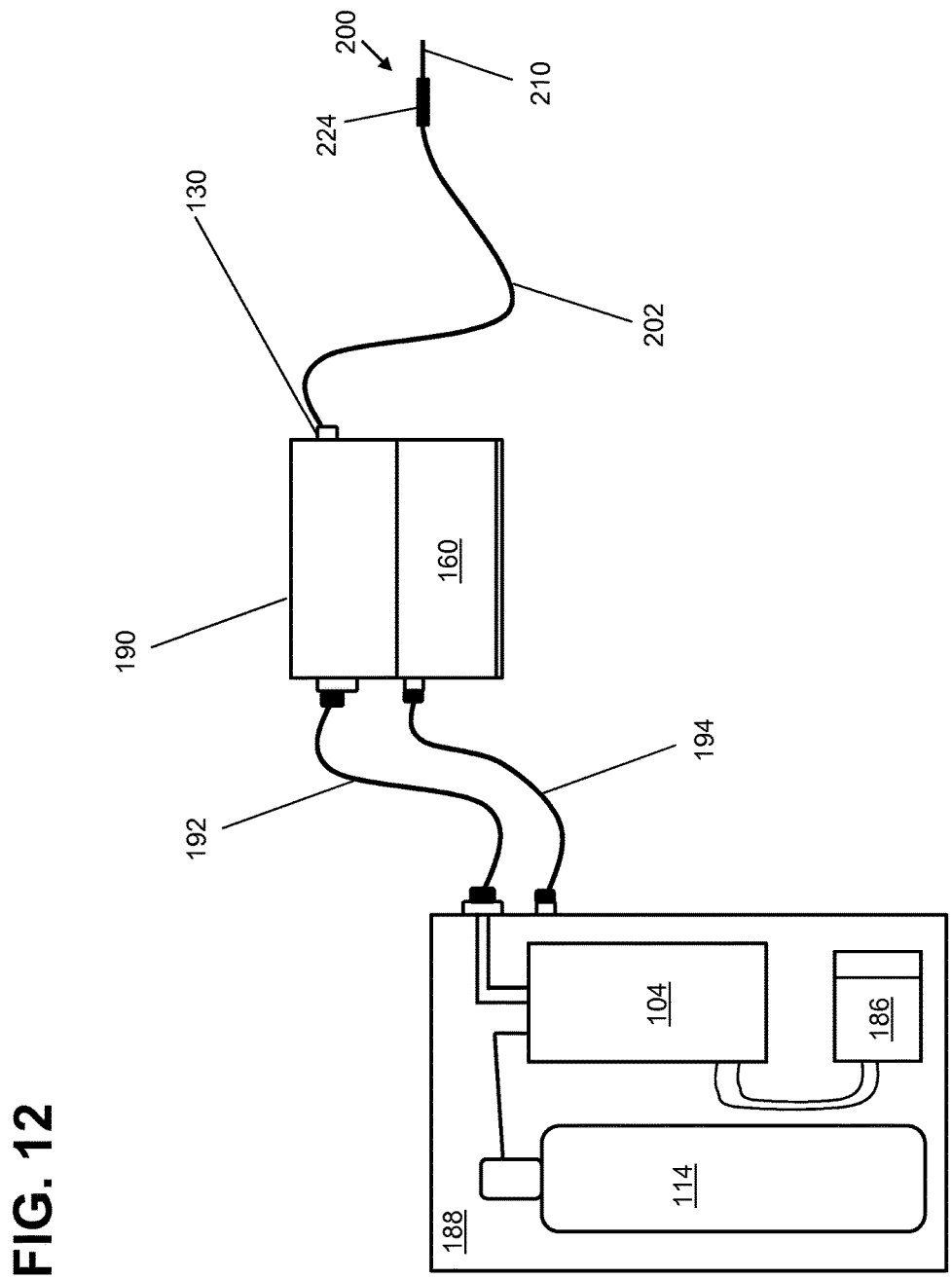
FIG. 12 shows a schematic illustration of a multi-component system in accordance with an embodiment of the invention.

As noted, the mechanical and electrical features of the cryogenic system may be substantially contained within an enclosure 102 that allows the system to be easily transported. As depicted in FIGS. 1 and 3, the enclosure 102 may include any mobile feature such as wheels 148, handles 150 (FIG. 3), and fixtures (or allow placement onto a cart having these features) so that the system can be transported to and from a treatment location. Further, any above-described device configuration may be connected to a satellite cryogen gas supply cart which contains any number of pressurized cylinders 114 (FIG. 8) for operation. Still further, as shown in FIG. 12, the system may be split into a cryogen cart 188 containing a cryogen gas pressurization cylinder(s) 114, the sub-cooling reservoir 104 and submerged sub-cooling coil 124, flow valves and various other components, which may be connected to a separate control console 190 via a single or multiple umbilical lines or connection points enabling cryogen connection 192 and electrical connection 194 communication between the two units for operation. In addition to features previously mentioned, electrical features contained within or on the enclosure 102 or console 190 may include, for example, probe and electrical interface connection ports 130, 152 for providing electrical control of the cryoprobe 200. This may include power on/off, heating/ thawing, and movement (deflection/steering) control. The electrical interface connection ports 152 shown on an exterior of the enclosure 102 of FIG. 1 may provide a connection between the enclosure 102 and probe 200 for supplying electronic communication, and control/monitoring as provided by control and monitoring system 160.

The above-described cryogenic system 100 creates an efficient heat transfer environment that extracts heat from targeted tissue creating a precise ice region. Return gas/ liquid mixture flows back through the return tubing and is re-collected in the reservoir, thus allowing for recycling of the unused cryogen without direct discharge into the surrounding environment, which is typical of gas based cryoablation systems.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 mm, or, more specifically, about 5 mm to about 20 mm," is inclusive of the endpoints and all intermediate values of the ranges of "about 5 mm to about 25 mm," etc.).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cryogenic system comprising:
   a reservoir containing a liquid cryogen;
   a heat exchange coil immersed in the liquid cryogen, the heat exchange coil being configured to cool a cryogen therein under pressure to produce a pressurized mixed phase cryogen within the heat exchange coil, wherein the cryogen is supplied to the heat exchange coil at a first pressure, and exits the heat exchange coil at a second, lower pressure;
   a cryo-device fluidly connected to the heat exchange coil by a supply line such that the pressurized mixed phase cryogen is delivered to the cryo-device; and
   a return line for conducting used cryogen away from the cryo-device, wherein the return line further conducts the used cryogen into the reservoir for collection.

2. The cryogenic system of claim 1, wherein the return line further conducts the used cryogen as bulk fluid into a cryogen gas pressure cylinder.

3. The cryogenic system of claim 1, wherein the return line further conducts the used cryogen to a heat exchanger venting system to warm and evaporate the cryogen prior to release into the atmosphere.

4. The cryogenic system of claim 1, further comprising a boiling chamber disposed at a distal tip of the cryo-device, the boiling chamber being configured to produce a drop in a pressure of the pressurized mixed phase cryogen within the boiling chamber.

5. The cryogenic system of claim 1, wherein the cryo-device is a cryoprobe.

6. The cryogenic system of claim 5, further comprising an enclosure in which the reservoir is disposed; and
wherein the cryoprobe further comprises:
an umbilical line coupled to the enclosure;
a probe handle coupled to the umbilical line; and
a probe shaft having an outer sheath disposed thereon, the probe shaft extending from the probe handle,
wherein the supply line is disposed within the umbilical, the probe handle, and the probe shaft, placing the cryoprobe in fluid communication with the heat exchange coil within the enclosure.

7. The cryogenic system of claim 6, further comprising a vacuum lumen disposed within the probe shaft, the vacuum lumen being in fluid connection with a vacuum pump disposed within the enclosure.

8. The cryogenic system of claim 1, further comprising at least one pressurized gas cryogen supply including:
a pressurized cryogen cylinder for supplying the cryogen to the heat exchange coil.

9. The cryogenic system of claim 8, wherein the at least one pressurized gas cryogen supply further comprises: two or more pressurized cryogen cylinder linked together in series or in parallel.

10. The cryogenic system of claim 8, further comprising at least one pressurized gas cryogen supply including: a low pressure cryogen supply and a compressor for pressurizing the cryogen.

11. The cryogenic system of claim 1, wherein the liquid cryogen contained within the reservoir is a liquefied gas cryogen and is one of: nitrogen, argon, oxygen, helium, hydrogen, propane, ethylene glycol, propanediol, or alcohol.

12. The cryogenic system of claim 1, further comprising:
at least one sensor for monitoring one or more of:
a pressure of a pressurized cryogen supplied to the heat exchange coil,
a pressure of the pressurized mixed phase cryogen output from the heat exchange coil,
a temperature of a pressurized cryogen supplied to the heat exchange coil,
a temperature of the pressurized mixed phase cryogen output from the heat exchange coil,
a temperature of the liquid cryogen contained within the reservoir,
a temperature of a tip of the cryo-device,
a flow rate of the pressurized cryogen supplied to the heat exchange coil,
a flow rate of the pressurized mixed phase cryogen output from the heat exchange coil,
a vessel fluid level in the reservoir, or
a vessel fluid level in a pressurized cryogen supply.

13. The cryogenic system of claim 12, further comprising:
a control center including a computer-readable storage medium which, when executed by a computing device, causes the computing device to carry out:
receiving feedback from the at least one sensor; and
based on the feedback, controlling at least one operation parameter of the cryogenic system, the at least one operation parameter including one or more of:
the pressure of the pressurized cryogen supplied to the heat exchange coil,
the pressure of the pressurized mixed phase cryogen output from the heat exchange coil,
the temperature of the pressurized cryogen supplied to the heat exchange coil,
the temperature of the pressurized mixed phase cryogen output from the heat exchange coil,
the temperature of the liquid cryogen contained within the reservoir,
the temperature of the tip of the cryo-device,
the flow rate of the pressurized cryogen supplied to the heat exchange coil,
the flow rate of the pressurized mixed phase cryogen output from the heat exchange coil,
the vessel fluid level in the reservoir, or
the vessel fluid level in the pressurized cryogen supply.

14. The cryogenic system of claim 2, wherein the cryogen gas pressure cylinder is used as a source for the cryogen supplied to the heat exchange coil.

15. The cryogenic system of claim 4, wherein the return line axially extends a first distance into the boiling chamber, and the supply line axially extends a second, longer distance into the boiling chamber, such that the supply line terminates nearer to the distal tip of the cryo-device than the return line.

16. The cryogenic system of claim 1, wherein the first pressure is between about 500 psi and about 2,500 psi.

17. The cryogenic system of claim 16, wherein the first pressure is between about 1,000 psi and about 1,500 psi.

18. The cryogenic system of claim 1, wherein the second, lower pressure is lower than the first pressure by a difference of about 200 psi or more.

19. A cryogenic system comprising:
a reservoir containing a liquid cryogen;
a heat exchange coil immersed in the liquid cryogen, the heat exchange coil being configured to cool a cryogen therein under pressure to produce a pressurized mixed phase cryogen within the heat exchange coil, wherein the cryogen is supplied to the heat exchange coil at a first pressure, and exits the heat exchange coil at a second, lower pressure; and
a cryo-device fluidly connected to the heat exchange coil by a supply line such that the pressurized mixed phase cryogen is delivered to the cryo-device, wherein the first pressure is between about 500 psi and about 2,500 psi.

20. A cryogenic system comprising:
a reservoir containing a liquid cryogen;
an enclosure in which the reservoir is disposed;
a heat exchange coil immersed in the liquid cryogen, the heat exchange coil being configured to cool a cryogen therein under pressure to produce a pressurized mixed phase cryogen within the heat exchange coil, wherein the cryogen is supplied to the heat exchange coil at a first pressure, and exits the heat exchange coil at a second, lower pressure;
a cryoprobe fluidly connected to the heat exchange coil by a supply line such that the pressurized mixed phase cryogen is delivered to the cryoprobe, wherein the cryoprobe further comprises:
an umbilical line coupled to the enclosure;
a probe handle coupled to the umbilical line;
a probe shaft having an outer sheath disposed thereon, the probe shaft extending from the probe handle, and
a vacuum lumen disposed within the probe shaft, the vacuum lumen being in fluid connection with a vacuum pump disposed within the enclosure,
wherein the supply line is disposed within the umbilical, the probe handle, and the probe shaft, placing the cryoprobe in fluid communication with the heat exchange coil within the enclosure.

* * * * *